United States Patent [19]

Saxena et al.

[11] Patent Number: 4,950,597
[45] Date of Patent: Aug. 21, 1990

[54] MODIFICATION OF CELLULOSE NORMALLY SYNTHESIZIED BY CELLULOSE-PRODUCING MICROORGANISMS

[75] Inventors: Inder M. Saxena; Eric M. Roberts; R. Malcolm Brown, Jr., all of Austin, Tex.

[73] Assignee: The University of Texas Board of Regents, Austin, Tex.

[21] Appl. No.: 198,784

[22] Filed: May 25, 1988

[51] Int. Cl.$^5$ .................. C12P 19/04; C12P 33/18; C12R 1/01; C12N 1/22

[52] U.S. Cl. ..................... 435/101; 435/84; 435/822; 435/823; 435/56; 435/252.1

[58] Field of Search ............... 435/101, 84, 822, 823, 435/56, 252.1

[56] References Cited

PUBLICATIONS

Shimwell, J. L. 1956. Transmutation of species in the genu Acetobacter, J. Inst. Brew.
Sarko, A., 1978, What is the Crystalline Structure of Cellulose?, TAPPI, 61:59–61.
Bureau, T. E. and R. M. Brown, Jr., 1987, In Vitro Synthesis of Cellulose II from a Cytoplasmic Membrane Fraction of Acetobacter Xylinium, Proc. Nat. Acad. Sci., U.S.A., 84:6985–6989.
Bertran, M. S. and B. E. Dale, 1985, Enzymatic Hydrolysis and Recrystallization Behavior of Initially Amorphous Cellulose, Biotechnol, Bioeng, 27:177–181.
Blanton, R. L. and H. D. Chanzy, 1985, Cellulose Detected in the Stalks of Protostelium Irregularies (Eumycatozoea), J. Protozool., 32(4): 740–741.
Brown, Jr., R. M., J. H. M. Wilson and C. Richardson, 1976, Cellulose Biosynthesis and Direct Measurement of the in vivo Process, Proc. Nat. Acad. Sci., U.S.A., 73:4565–4569.
Brown, Jr., R. M., C. H. Haigler, J. Suttie, E. Roberts, C. Smith, T. Itoh and K. Cooper, 1983, The Biosynthesis and Degradation of Cellulose, J. Appl. Polymer Sump, 37:33–78.
Reference AV Bureau, T. E. and R. M. Brown, Jr. 1987. In vitro synthesis of cellulose II from a cytoplasmic membrane fraction of Acetobacter xylinum. Proc. Nat. Acad. Sci. USA 84:6985–6989.
Reference AW Canale-Parola, E. R., Borasky and R. S. Wolfe, 1961, Studies on Sarcina Ventriculo, III, Localization of Cellulose, J. Bacteriol, 8:311–318.
Reference AX Canale-Parola, E. and R. S. Wolfe, 1964, Synthesis of Cellulose by Sarcina Ventriculi, Biochim. Biophys. Acts 82:403–405.
Reference AY Cronshaw, J. A. Myers and R. D. Preston, 1958. A chemical and physical investigation of the cell walls of somemarine algae. Biochim. Biophys. Acta, 27:89–103.
Reference AZ Deinema, M. H. and L. P. T. M. Zevenhuizen, 1971, Formation of Cellulose Fibrils by Gram-Negative Bacteria and Their Role in Flocculation, Arch. Mikrobiol., 78;42–57.
Reference BA DeLey, J., 1961, Comparative Carbohydrate Metabolism and a Proposal for a Phylogenetic Relationship of the Acetic Acid Bacteria, J. Gen. Microbiol., 24:31–50.

(List continued a next page.)

Primary Examiner—Ronald W. Griffin
Assistant Examiner—Pamela S. Webber
Attorney, Agent, or Firm—Arnold, White & Durkee

[57] ABSTRACT

The present invention involves a process for screening for and isolating spontaneously occurring or induced cellulose II-producing microorganisms. The process comprises a series of steps in various embodiments. Initially, cellulose-producing microorganisms from a first culture are plated out on a nutrient agar plate. The nutrient agar plate is then incubated to facilitate formation of colonies from single microorganisms. Samples of liquid nutrient medium are then inoculated with microorganisms from colonies having a smooth configuration, as compared to the usual rough colony configuration. The inoculated samples are then aerobically incubated to facilitate microorganism proliferation and pellicle formation. From these incubated samples are selected microorganisms, which, after a cultivation period, have proliferated but not formed a pellicle. Said selected microorganisms produce cellulose II instead of the cellulose I produced by pellicle-forming organisms.

16 Claims, 7 Drawing Sheets

OTHER PUBLICATIONS

Reference BB DeLey, J. M. Gillis and J. Swings, 1984 Family VI, Acetobacteraceae, In: "Bergey's Manual of Systematic Bacteriology", vol. 1 (N. R. Krieg and J. G. Holt, eds.), Williams and Wilkins, Baltimore and London, pp. 267-274.

Reference BC Dillingham, E. O., A. G. Jose and D. T. Knuth (1961), Cellulose and Cellulose-Free Cell Production by Acetobacter Xylinum, (Abstract). Bact. Proc, 61st Ann. Meeting, p. 67.

Reference BD Dodson, J. R. and J. M. Aronson, 1978,, Cell Wall Composition of Enteromorpha Intestinalis, Bontanica Marina, 21:241-246.

Reference BE Forge, A., 1977, Electron Microscopy of a Non-Pellicle-Forming Strain of Acetobacter Xylinum, Ann. Bot., 41:455-460.

Reference BF Frei, E. and R. D. Preston, 1961, Variants in the Structural Polysaccharides of Algal Cell Walls, Nature, 192:939-943.

Reference BG Frei, E. and R. D. Preston, 1963, Clay Minerals and the Cell Walls of Seaweeds, Proc. Leads Phil. Lit. Soc. (Scientific Section), 9(4):101-111.

Reference BH Gezelius, K., 1959, The Ultrasonicstructure of Cells and Cellulose Membranes in Acrasiae, Exp. Cell Res., 18:425-453.

Reference BI Gezelius, K. and B. G. Ranby, 1957, Morphology and Fine Structure of the Slime Mold Dictyostelium Discoidium, Exp. Cell Res., 12:265-289.

Reference BJ Haigler, C. and M. Benziman, 1982, Biogenesis of Cellulose I Microfibrils Occurs be Cell-Directed Self Assembly in Acetobacter Xylinum, In: Cellulose and Other Natural Polymer Systems: Biogenesis, Structure and Degradation. R. M. Brown, Jr., ed. Plenum Press, New York and London.

Reference BK Henley, D. 1961, A Macromolecular Study of Cellulose in the Solvent Cadoxen, Arkiv Kemi, 18:327-392.

Reference BL Hestrin, S. and M. Schramm, 1954, Synthesis of Cellulose by Acetobacter Xylinum, II, Preparation of Freeze-Dried Cells Capable of Polymerizing Glucose to Cellulose, Bioch. J., 58:345-352.

Reference BM Hieta, K., S. Kuga and M. Usuda, 1984, Electron Staining of Reducing Ends Evidences a Parallel Chain Structure in Valonia Cellulose, Biopolymers, 23:1807.

Reference BN Horii, F., A. Hirai and R. Kitamaru, 1987, Cross-Polarization-Magic Angle Spinning Carbon-13 NMR Approach to the Structural Analysis of Cellulose, In: The Structure of Cellulose: Characterization of the Solid State (A.C.S. Symposium Series 340), R. H Atalla, ed., American Chemical Society, Washington, D.C.

Reference BO Huizing, H. J., H. Reitma and J. H. Sietsma, 1979, Cell Wall Constituents of Several Siphonous Green Algae in Relation to Morphology and Taxonomy, Br. Phycol. J., 14:25-32.

Reference BP Kolpak, F. J. and J. Blackwell, 1978, The Morphology of Regenerated Cellulose, Textile Res. J., 48:458-467.

Reference BQ Kulshreshtha, A. K. 1979, A Review of the Literature on the Formation of Cellulose IV, Its Structure, and Its Significance in the Technology of Rayon Manufacture, J. Textile Inst., 70(1):13-18.

Reference BR Muhlethaler, K., 1956, Electron Microscopic Study of the Slime Mold Dictyostelium Discoidium, Am. J. Bot., 43:673-678.

Reference BS Myers, A. and R. D. Preston, 1959, Fine Structure in the Red Algae, II, The Structure of the Cell Wall of Rhodymenia Palmata, Proc. Roy. Soc. B., 150:447-455.

Reference BT Myers, A., R. D. Preston and G. W. Ripley, 1955, Fine Structure in the Red Algae, I, X-Ray and Electron Microscopic Investigation of Griffithsia Flosculosa, Proc. Roy. Soc. B, 144:450-459.

Reference BU Nicolai, E. and R. D. Preston, 1952, Cell Wall Studies in the Chlorophycease, I, A General Survey of Submicroscopic Structure in Filamentous Species, Proc. Roy. Soc. B, 140:244-274.

Reference BV Raper, K. B. and D. I. Fennell, 1952, Stalk Formation in Dictyostelium, Bull. Torry Bot. Club, 79(1):25-51.

Reference BW Robinson, D. G. and R. D. Preston, 1972, Polysaccharide Synthesis in Mung Bean Roots—An X-Ray Investigation, Biochim. Biophys. Acta, 273:336-345.

Reference BX Roelofsen, P. A., V.ch. Dalitz and C. F. Wijnman, 1953, Constitution, Submicroscopic Structure and Degree of Crysdtallinity of the Cell Wall of Halicystis Osterhouti, Biochim. Biophys. Acta, 11:344-352.

(List continued a next page.)

OTHER PUBLICATIONS

Reference BY Sarko. A. 1978. What is the crystalline structure of cellulose? TAPPI 61:59–61.

Reference BZ Schell, J. and J. De Ley, 1962, Variability of Acetic Acid Bacteria, Antonie va Leeuwenhoek, 28:455–465.

Reference CA Schramm, M. and S. Hestrin, 1954, Factors Affecting Producing of Cellulose at the Air–Liquid Interface of a Culture of Acetobacter Xylinum, J. Gen. Microbiol., 11:123–129.

Reference CB Shimwell, J. L., 1956 Transmutation of Species in the Genus Acetobacter., J. Inst. Brew., 62:339–343.

Reference CC Shimwell, J. L. and J. C. Carr, 1960. Derivation in Non–Acetifying "Quasi–Acetobacters" from a True Acetobacter Strain and Vice Versa, Antonie van Leeuwenhoek, 26:169.

Reference CD Sisson, W., 1938, The Existence of Mercerized Cellulose and Its Orientation in Halicystis as Indicated by X–Ray Diffraction Analysis, Science, 87:350.

Reference CE Sisson, W., 1941, Some X–Ray Observations Regarding the Membrane Structure of Halicystic. Contr. Boyce Thomp. Inst., 12:31–44.

Reference CF Sleytr, U. B. and A. W. Robards, 1977, Plastic Deformation During Freeze–Cleavage: Areview J. Microsc., 110(1):1–25.

Reference CG Steel, R. and T. K. Walker, 1957, A Comparative Study of Cellulose–Producing Cultures and Celluloseless Mutants of Certain Acdtobacter spp. J. Gen. Microbiol., 17:445–452.

Reference CH Wiley, J. H. and R. H. Atalla, 1987, Raman Spectra of Celluloses, In: The Structure of Cellulose; Characterization of the Solid State (A.C.S. Symposium Series 340), R. H. Atalla, ed., American Chemical Society, Washington, D.C.

Reference CI Valla, S. and J. Kjosbakken, 1982, Cellulose–Negative Mutants of Acetobacter Xylinum, J. Gen. Microbiol., 128:1401.

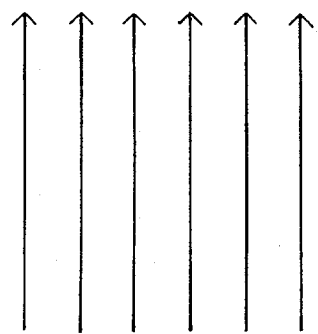
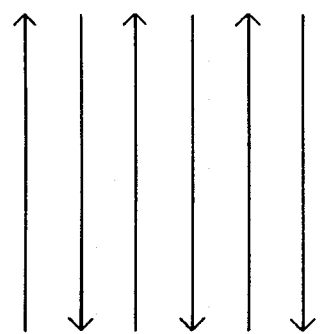
FIG. 1A     FIG. 1B
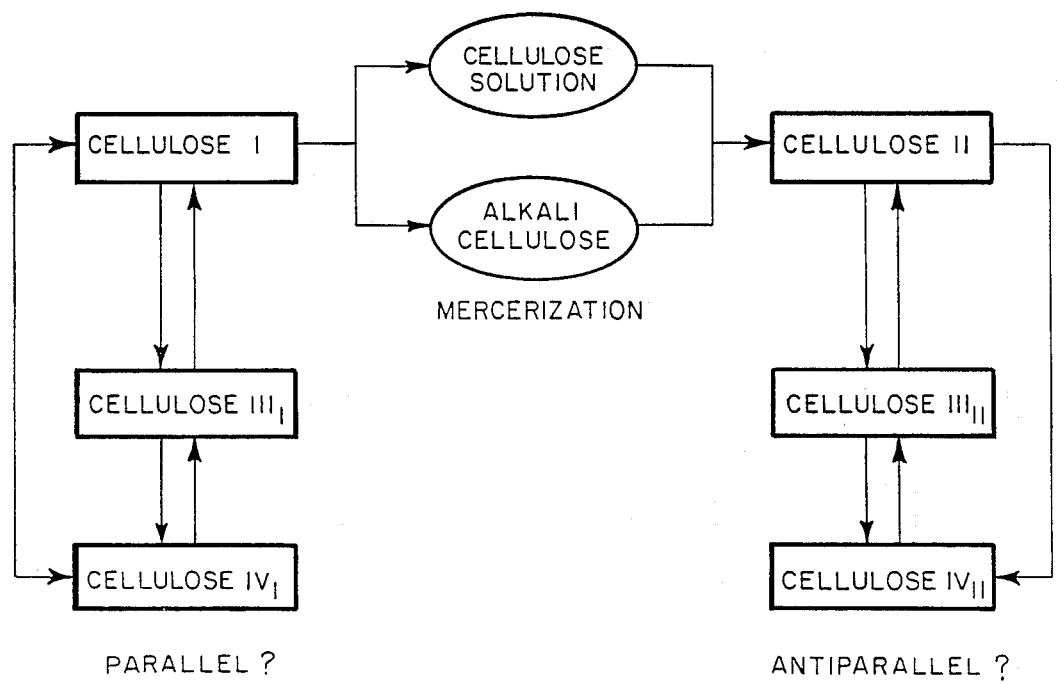
BASED ON ELLEFSEN et el., 1964
FIG. 2

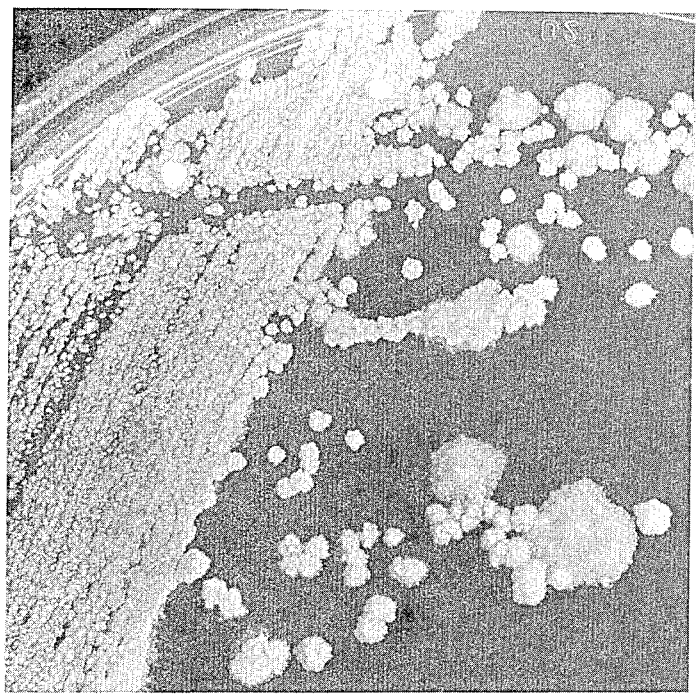
FIG. 3A1
FIG. 3A2
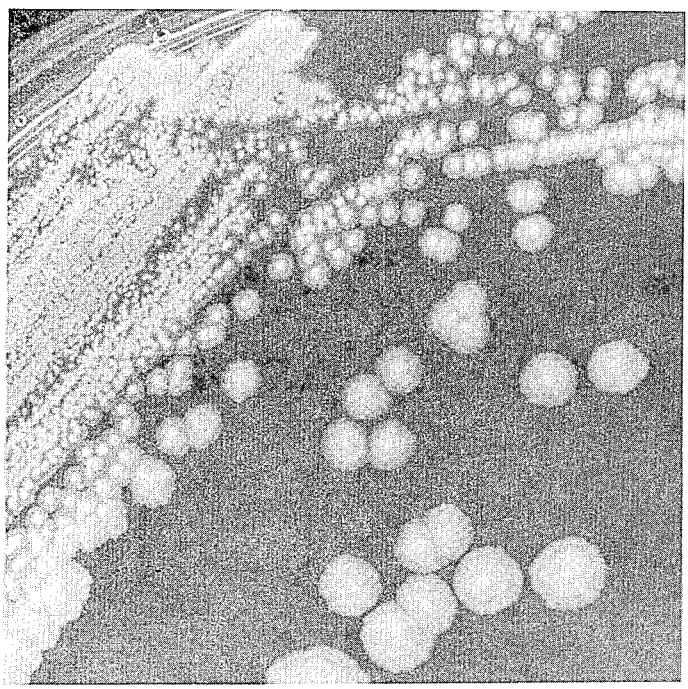
FIG. 3B1
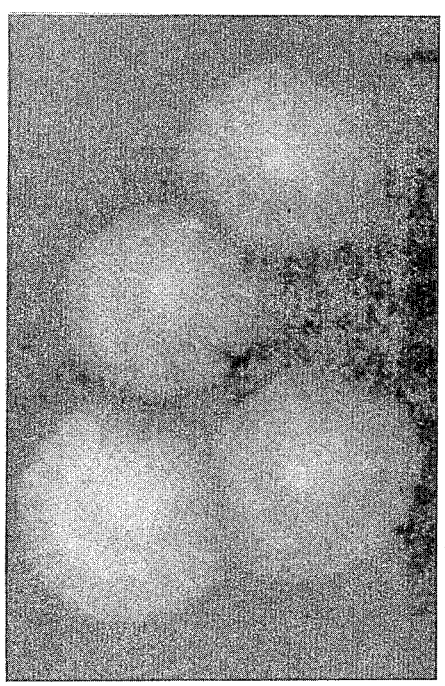
FIG. 3B2

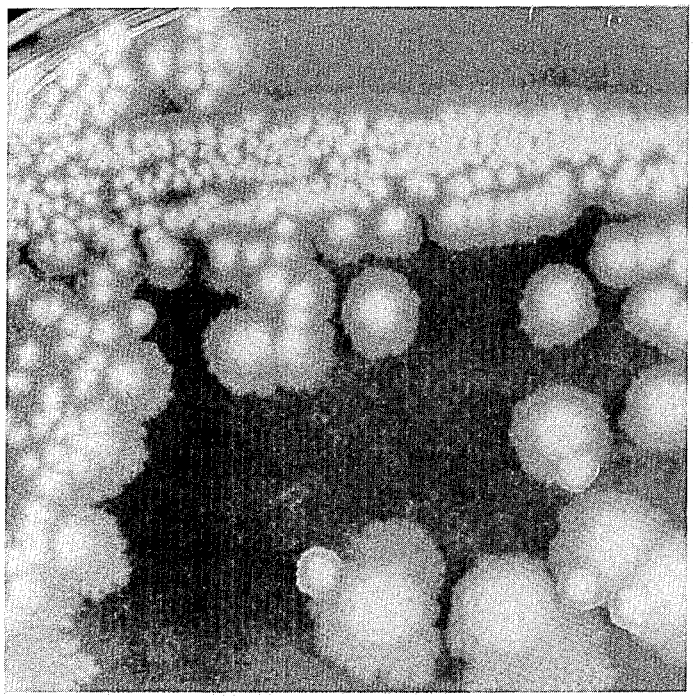
FIG. 3C1
FIG. 3C2
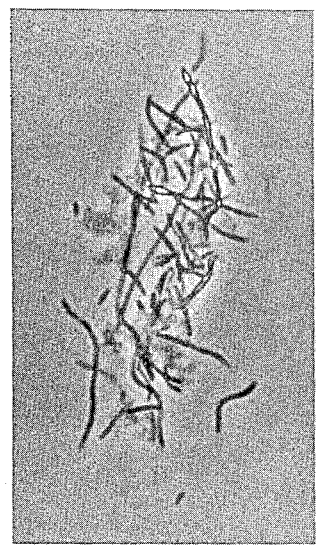
FIG. 4A
FIG. 4B

MODIFICATION OF CELLULOSE NORMALLY SYNTHESIZIED BY CELLULOSE-PRODUCING MICROORGANISMS

BACKGROUND OF THE INVENTION

The present invention relates to the modification of cellulose normally synthesized by cellulose-producing microorganisms. This modification results from the selection of mutant microrganisms which form cellulose II rather than the usual native cellulose (cellulose I).

Cellulose is produced be a variety of microorganisms including the genera *Acetobacter, Rhizobium, Alcaligenes, Agrobacterium,* and *Sarcina* (see, for example, Deinema and Zevenhuizen, 1971 or Brown, et al., 1983). The growth of these cellulose-producing microorganisms with the production of cellulose occurs when said microorganisms are cultivated in an appropriate nutrient medium.

Appropriate nutrient media of the present invention generally include standard nutrient media such as GYC which contains (g/liter of distilled water): yeast extract, 10.0: D-glucose, 50.0; $CaCO_3$, 30.0, and agar, 25. Various alternatives such as replacements for glucose or yeast extract, and the omission of agar or $CaCO3$ are usable and well known to those skilled in the art (De Ley et al., 1984). The preferred nutrient medium used directly or with modifications described herein was that first described by Hestrin and Schramm (Hestrin and Schramm, 1954). A standard Schramm-Hestrin medium (SH medium) used herein contained (g/L): D-glucose, 20; peptone, 5; yeast extract, 5; 5; dibasic sodium phosphate, 2.7, and citric acid monohydrate, 1.15. The pH of the medium may be adjusted to between 3.5 and 5.5 with HCl or it may be used without adjustment.

The cellulose produced by *Acetobacter xylinum* (formerly known as *Acetobacter aceti* subsp. *xylinum* and reclassified in the 1984 Bergey's Manual (DeLey, et al., studied. In the present application, the primarily studied cellulose-producing microorganism is termed "*Acetobacter xylinum*" (*A. xylinum*). It is understood that these several names may be used to indicate the same organism.

Alterations of the cellulose fibrils produced by microorganisms by agents such as carboxymethyl cellulose (CMC) or by dyes such as Congo Red or Tinopal have been previously observed by electron microscopy (see, for example, Haigler and Benziman, 1982). However, nowhere before the present invention has any substance or method been found or suggested to initiate the microbial production of cellulose II. (Chemical conversion of cellulose I to Cellulose II after synthesis is, however, widely known.)

*Acetobacter xylinum* (now classified under *A. pasteurianus* and *A. hansenii* in De Ley et al., 1984) is a gram negative aerobic bacterium that produces an extracellular ribbon of cellulose (Brown et al., 1976). When grown in stationary liquid culture, the ribbons of cellulose produced by individual cells entangle, eventually forming a thick mat of cellulose called a pellicle at the surface of the medium. Although all cellulose is a beta-1,4 linked polymer of D-glucopyranose, it occurs in several distinct crystalline forms known as allomorphs or polymorphs (briefly reviewed in Sarko, 1978). Five different cellulose allomorphs are currently known: cellulose I, cellulose 11, cellulose 111, cellulose IV, cellulose X. Nearly all organisms which synthesize cellulose, including *A. xylinum,* produce the allomorph cellulose I or "native cellulose". Although a few organisms have been claimed to synthesize cellulose II, the present invention involves the first confirmed description of in vivo synthesis of cellulose II by any prokaryote, particularly Acetobacter.

Variability within the Acetobacter genus has been extensively discussed in the microbiological literature. Some workers (e.g., Shimwell and Carr, 1960) have reported that both biochemical and colony morphology mutations were "extraordinarily facile" and of "kaleidoscopic rapidity and effect". In contrast, Schell and De Ley (1962) state that the rate of mutation is comparable to other genera of bacteria. These conflicting beliefs are reflected in two different concepts about what constitutes the *Acetobacter* genus. On one hand, workers such as Shimwell have proposed that all acetic acid bacteria are merely strain variations within two biotypes *Gluconobacter oxydans* and *Acetobacter aceti.* On the other hand De Ley (1961) and others have proposed that a phylogenetic derivation of species whereby all extant strains have been derived from ancestral strains primarily by the deletion of various enzymes.

It has been reported that many strains of *Acetobacter* can lose the ability to produce cellulose. (Reversion of putative "non-cellulose" producers has also been claimed, e.g. Shimwell, 1956). Such cel- variants can arise spontaneously, or be induced by various physical or chemical treatments.

Cellulose deficient *Acetobacter* strains (referred to in this paper as "cel-" strains) were reported in 1954 by Schramm and Hestrin. These workers noted that when serially transferred in shaken liquid cultures, *A. xylinum* loses its ability to synthesize cellulose. Such changes were generally correlated with changes in colony morphology of cells grown on nutrient agar plates (i.e., the formation of smooth colonies). Schramm and Hestrin proposed that shaking cultures conferred a selective advantage to naturally occurring cellulose deficient mutants within a population leading to an eventual loss of the wild type. The wild type, however, was selected for in static liquid cultures because the cellulose pellicle formed at the surface of the medium, kept wild type cells near their oxygen source.

Following this first report, cellulose deficient forms have been isolated from many strains by numerous methods. Creedy et al. (1954) isolated cellulose deficient mutants of A. acetigenum by treatment with sodium arsenate, while Steele and Walker (1957) found that variations in culture medium (notably the use of ethanol as a carbon source) was also correlated with the loss of cellulose production. Since this time, other reports of cel- forms have appeared. It is not clear if these agents act as mutagens or if they act merely as selection media for spontaneously occurring variants.

Some evidence suggests that "cellulose deficient" mutants of *Acetobacter* may actually produce small amounts of cellulose. Valla and Kjosbakken (1982) reported the presence of "cel-" mutants which have alterations in the gene(s) involved in cellulose synthesis, In the same paper, these authors report that cel- cells can form aggregates that are dispersed by cellulase. In addition, they report that 50% of these mutants can be induced to form cellulose by treatment with tetracycline. (The allomorph that these mutants produce was not determined.) It is suggested that the mutation is not in the structural gene(s) for cellulose biosynthesis, but in some other accessory gene necessary for complete expression of the cel+ phenotype.

In 1977, Forge published a study on "non-pellicle forming" strains of *A. xylinum* isolated from shake cultures. While these cells do not form a pellicle, Forge claimed to have identified short fibrils associated with the outer membrane using freeze-etch electron microscopy. Although elongated structures are present in his micrographs, these appear to be very similar to plastic deformation artefact (Sleytr and Robards, 1977). Forge also examined non-pellicle forming cultures with x-ray diffraction. In a few cases, a faint cellulose I pattern was observed. Forge concluded that while his strain did not form a pellicle, small amounts of cellulose I were synthesized, perhaps by enzymes that had been dispersed over the entire membrane surface. This is the only report known to the Applicants that discusses the x-ray diffraction pattern produced from non-pellicle forming cultures.

As mentioned, the cellulose molecule is defined not only by its chemical constitution, beta-1,4 linked glucopyranose, but also by the manner in which these molecules are packed together into crystalline forms. Currently, five distinct crystalline allomorphs of cellulose have been identified by their x-ray diffraction patterns: cellulose I,II,III,IV, and X (e.g., Ellefsen and Tonnesen, 1971). These allomorphs may also be grouped according to chain polarity, as described later. The unique packing of glucan chains into cellulose crystallites can be identified by a variety of techniques. Older cytochemical methods for distinguishing cellulose allomorphs using iodine staining (e.g., Roelofsen, 1959) are notoriously unreliable and have been replaced by other methods which yield unique "fingerprints" for cellulose I and II and thus allow these allomorphs to be distinguished. The distinctive infrared (IR) spectra of cellulose I and II are described in Blackwell and Marchessault (1971). As described by these authors, "For cellulose II ... the -OH stretching region is distinctively different from the equivalent region in cellulose I. This allows for easy identification of the two forms" (p.17). Crosspolarized magic angle spinning 13C nuclear magnetic resonances (CP/MAS 13C NMR) provides another method for the identification of cellulose allomorphs. As described in Horii et al. (1987), "... the C1 and C4 resonances [of regenerated cellulose] split into doublets with equivalent intensities. This is in contrast to the case of native cellulose, reflecting that the crystal structure of regenerated cellulose is cellulose II" (p. 128). Raman spectroscopy may also be used to distinguish the allomorphs of cellulose. For example, Wiley and Atalla (1987) note that although the spectra of cellulose I samples derived from various sources may vary somewhat,". . . in the spectrum of cellulose II . . . the frequency and number of peaks is significantly different" (p. 164 and spectra p. 162). Electron diffraction has been used to study crystalline materials in general, and the various cellulose allomorphis in particular (French, 1985). The technique of neutron diffraction is theoretically also suited for cellulose crystal studies (French, 1985). The most widely used technique is x-ray diffraction; it allows the determination of distances separating planes of atoms (called d-spacings) in the crystals. These d-spacings are unique for any given crystal form and thus act like a fingerprint for each of the cellulose allomorphs (Tripp and Conrad, 1972). Actual d-spacing values vary somewhat from sample to sample, especially for larger values. Short, general reviews of cellulose polymorphism can be found in Tripp and Conrad (1972), Sarko (1978) and Ellefsen and Tonnesen (1971).

Of the cellulose allomorphs, cellulose I ("native cellulose") is the form found naturally occurring in nearly all plants. Cellulose II, also known as "hydrate" cellulose is well known industrially. For example, both rayon and mercerized cellulose are forms of cellulose II. It can be generated by precipitation from solution, by treatment of cellulose I with strong swelling agents such as 24% KOH, and other means. Cellulose I and cellulose II are the commercially dominant allomorphs of cellulose.

The glucan chains which comprise native cellulose (cellulose I) are thought by most workers to exist in a "parallel" orientation (FIG. 1), i.e. all the reducing ends of a glucan chain represented by arrowheads in the diagram are pointed in the same direction. In contrast, most workers believe that cellulose II exists in an antiparallel form (reducing ends of the glucan chains having a statistically random orientation within a fibril). This prevailing idea is not universally accepted. French (1985) has pointed out that the R values (measures of fit of a given model with x-ray diffraction data) for a parallel and antiparallel chain cellulose I do not completely eliminate either model of chain polarity. Hieta, et al. (1984) have recently shown by cytochemical means that all the reducing ends of Valonia microfibrils are clustered on one end of the fibril, thus lending support to the idea of a parallel chain arrangement for cellulose I in this organism. Sakthivel, et al. (1987) have recently proposed that both a parallel and antiparallel cellulose II may exist.

Several allomorphs of cellulose exist in two subforms (e.g. $III_I$ and $III_{II}$) depending on which "parent" allomorph gave rise to it (Sarko, 1978). Thus, the parallel form of cellulose III (generated from cellulose I) is designated $III_I$, while the antiparallel form (made from cellulose II) is designated $III_{II}$. Although the defraction patterns of these subforms are indistinguishable, they can be identified because if the transition is reversed, only the original parent will be produced. This property is referred to as "memory".

Interconversion of the various cellulose allomorphs is summarized in FIG. 2. This figure also illustrates the irreversible transition of cellulose I to cellulose II. Cellulose II is the more thermodynamically stable form of cellulose, in part due to increased hydrogen bonding between stacks of glucan chains (French 1985).

Relative thermodynamic stability and chain polarity have important implications for the in vivo biosynthesis of cellulose. It is generally accepted that a single cellulose synthase enzyme will polymerize glucan chains unidirectionally, i.e., that all reducing ends will emerge from the enzyme pointing in the same direction. When numerous cellulose synthase enzymes are grouped together, such an arrangement has been suggested to facilitate the "cell directed self assembly" of a parallel chain polymer (Haigler and Benziman, 1982). This idea is implicit even in the earliest x-ray diffraction studies of cellulose structure; for example, Meyer and Mark (1928) originally proposed a parallel chain arrangement simply because they felt it was unlikely that two enzymes (one type synthesizing reducing end first, the other, nonreducing end first) could exist. It is of interest that the cellulose produced by essentially all plants (cellulose I) should be a thermodynamically less stable form of this polymer.

Over the last 50 years, a relatively small number of organisms has been suggested to make native cellulose II. These organisms ranged from bacteria to slime molds to algae. Each of these claims will be reviewed in the following section and are summarized in Table 1.

TABLE 1

ORGANISMS SUGGESTED TO PRODUCE NATIVE CELLULOSE II

| Organism | Citation |
|---|---|
| Halicystis grandis | Sisson (1938, 1941) |
| H. ovalis | Sisson (1938, 1941) |
| H. parlvula | Sisson (1938, 1941) |
| H. osterhoutii | Sisson (1938, 1941) |
| Oomyces sp. | Frey-Wyssling (1976) |
| Dictyostelium discoidium | Raper & Fennell (1952) |
| D. discoidium | Gezelius and Ranby (1957) |
| D. discoidium | Muhlethaler (1956) |
| Various green algae | Nicolai & Preston (1952) |
| Sarcina ventriculi | Kreger (in Roelofsen, 1959) |
| Enteromorpha intestinalis | Dodson and Aronson (1978) |

In 1938 and 1941, Sisson published studies on the cell walls of the green alga Halicystis. He suggested that the four species he examined, H. grandis, H. osterhoutii, H. ovalis, and H. parvula, contained the cellulose II allomorph although other crystalline material with a reflection around 13 Angstroms (A) (later ascribed to a crystalline 1,3-xylan; see Preston, 1974) was also present. These components were revealed only after sequential extraction with HCl followed by other solvents such as NaOH.

Halicystis has been subsequently investigated by several groups. Roelofsen et al. (1953), examined the walls of these cells and concluded that a xyloglucan (and not simply cellulose) was present. Frei and Preston (1961) Were able to isolate a cellulosic component from the wall, but felt that this material might result from chemical treatment causing crystallization of a previously "paracrystalline" component from the wall. Most recently, Huizing et al. (1979) reported that the walls of the gametophyte of Derbesia tennuissima (taxonomically equivalent to Halicystis) "failed to show any crystallinity by x-ray analysis, even after prolonged boiling in dilute acid". As summarized by Preston (1974), "it is still a moot point whether the glucan [from Halicystis] is cellulose II . . .".

In the 1950's naturally occurring cellulose II was reported to occur in a number of organisms. Raper and Fennel (1952) reported that intact sorophores of the cellular slime mold Dictyostelium discoidium gave weak fiber diagrams with two equatorial reflections at 4.05 A and 4.41A. Dictyostelium cellulose was also examined by Muhlethaler in 1956. Although untreated sorophores gave weak patterns, equatorial reflections of 4.03A, 3.33 A, and 2.56 A could be identified. Boiling the stalks in 5% $H_2SO_4$ followed by 5% NaOH, however, resulted in the loss of these reflections and the appearance of reflections that appeared to correspond to cellulose I alone. Muhlethaler (1956) concluded that the high temperature cleaning treatment caused a conversion of cellulose II to cellulose I. (Contemporary ideas of cellulose thermodynamic stability make such a transition seem unlikely). Gezelius and Ranby (1957) examined two strains of this same genus. In stalks cleaned by boiling in 1N NaOH or by 1 N NaOH followed by boiling in 2.5% $H_2SO_4$, the major reflections of cellulose I together with a 7.17 A reflection attributed to cellulose II was observed. From this data, the authors concluded that cellulose was present as "a partly mercerized cellulose of very low crystalline order" and noted that "the problem will be further studied". In 1959, Gezelius published his observations on Acytostelium, an acellular slime mold. In untreated stalks from this organism, reflections of 10 A, 4.6 A and 3.85 A were observed. These reflections could not be attributed to any known cellulose allomorph. After purification by boiling IN NaOH, the diffraction pattern of native cellulose was obtained along with a persistent diffuse ring at approximately 10 A. Despite the fact that no reflections of mercerized cellulose were seen, the author stated that "the results agree with those obtained with Dictyostelium discoidium . . ." More recently, Blanton and Chanzy (1985) used electron diffraction to demonstrate that the stalk of Protostelium irregularis is composed of cellulose I.

During the 1950's, cellulose and other wall components of algae were also vigorously investigated. Nicolai and preston (1952) investigated nearly 60 species of green algae using a variety of techniques, and especially x-ray diffraction. Their results suggested that the algae investigated could be placed into three groups. The cell walls of the first group were composed of highly crystalline cellulose I microfibrils usually arranges in the wall as cross parallel lamellae. Algae of this first group were found primarily in the order Cladophorales with a few representatives from the order Siphonales.

The second group contained the bulk of the algae examined. The walls of this group contained poorly crystalline material whose d-spacings approximated those of cellulose II. The authors noted, however, that they could not rule out the possibility that this material was cellulose derivative and not cellulose II. (The hesitancy to conclude that cellulose II was absolutely present is emphasized by Cronshaw et al. (1958) when group 2 is defined as those algae certainly not containing cellulose I). The third wall group originally described by Nicolai and Preston was a small group of algae whose x-ray patterns were uninterpretable. At the time that these studies were carried out, the results were considered to follow taxonomic lines.

The presence of native cellulose II was also suggested for the red alga Griffithsia flosculosa (Myers et al., 1955) although this contention was subsequently moderated (Myers and Preston, 1959).

The degree of caution expressed by Preston and co-workers on the occurrence of native cellulose II among the algae proved to be well founded. In 1963, Frei and Preston showed that some of the putative "cellulose II" reflections observed in previous studies persisted even after ashing. (Ashing would destroy any of the cellulose allomorphs). It was then observed that small clay particles adhering to the walls of algae collected from nature exhibited x-ray reflections similar to those of cellulose II. In addition, the flat clay platelets lay orientated on the cell walls, a fact which also explains why the x-ray patterns reported in previous papers were arranged in uniplanar orientations. (Such clays exist as small platelets and thus would not be present for material cultured in natural seawater that had been filter sterilized through 0.22 micron filters).

Although Frei and Preston (1963) did not reexamine all the species discussed in previous reports, the identification of clays on algal walls renders the identification of cellulose II by Nicolai and Preston (1952), and all others using walls collected from nature, uncertain. This concern extends even to material which has been closely examined for contaminants or has been soaked overnight in dilute acids to remove mineral incrustations. However, it is not possible to completely dismiss all of these claims since it was reported that the alga *Enteromorpha intestinalis,* cultured in the absence of such clay particles, may contain cellulose II (Dodson and Aronson, 1978).

Synthesis of cellulose II by a Prokaryote has also been suggested. Kreger, cited in Roelofsen (1959), examined "mechanically cleaned walls" (thus, apparently avoiding the problems of chemically induced conversion of cellulose I to cellulose II) from the bacterium *Sarcina ventriculi.* This material was claimed to show a cellulose II x-ray diagram, although this data was apparently never published. Chemical and enzyme digestion studies by Canale-Parola et al. (1961) and Canale-Parola and Wolfe (1964) strongly suggest that cellulose is associated with the bacterial packets, although the allomorph was not determined. Subsequent studies in the laboratory of the Applicants suggests that *S. ventriculi* strains obtained from the American Type Culture Collection of bacteria (ATCC) do produce the cellulose II allomorph.

Finally, it should be noted that in vitro cellulose synthesis by cell-free preparations of *Acetobacter xylinum* have recently been shown to produce the cellulose II allomorph (Bureau and Brown, 1987). This presumably results from the disruption of closely associated cellulose synthase enzymes and the consequent loss of cell directed assembly of the crystalline cellulose ribbon. In the absence of such control, the thermodynamically stable allomorph will form. Until this time, however, it has never been suggested that intact cells of *Acetobacter* can produce cellulose II. Commercial Production of Cellulose II The primary allomorphs of cellulose used industrially are cellulose I and cellulose II. Commercial products composed of cellulose II or substantial fractions thereof) include "rayon" and "mercerized cellulose". Both rayon and mercerized cellulose are manmade products derived from natural cellulose I such as that from wood pulp or cotton.

Some of the major processes for manufacturing cellulose II include the viscose process, the cuprammonium process, and the saponified cellulose acetate process (see Joseph, 1977; Moncrieff, 1975, or related textbook). These are briefly described below.

The viscose process involves steeping cellulose I (e.g., wood pulp) in alkali solution to form soda cellulose. This material is shredded, aged, and then treated with carbon disulfide which forms a bright orange intermediate called sodium cellulose xanthate. The xanthate is then dissolved in dilute NaOH, aged, and extruded through a spinerette system into an acid bath to form fibers of cellulose II. (See Moncrieff, 1975).

In the production of cuprammonium rayon, cellulose is bleached and dissolved in a solution of ammonia, copper sulfate and NaOH. This viscous blue solution is then spun into water, acidified and cleaned. The resulting cellulosic fibers consist of cellulose II.

Another method that has been used to produce highly crystalline cellulose II involves the deacetylation of cellulose acetate. This saponified cellulose process begins with cellulose acetate treated with alkali. The acetyl groups react to form sodium acetates which then split off. They are replaced by hydroxyl groups leaving cellulose II.

Mercerization is a chemical finishing process for cellulose textiles in which cellulose I is converted into cellulose II. This process, consists of treating wetted fabric with alkali (typically 16-27% NaOH) and, after a suitable amount of time, washing the fabric.

Each of the processes described above ultimately involve the conversion of cellulose I to cellulose II. In general, cellulose II products have improved dye uptake, higher strength, and greater moisture absorbance than the cellulose II of cotton fibers (Joseph, 1977). The actual I5 properties of cellulose II fibers are dependent on how they are produced and processed. Advantages of Native Synthesis of Cellulose II The present invention involves the native synthesis of cellulose II by *Acetobacter xylinum.* Although the organism described in the current report does not produce large quantities of cellulose compared to the wild type, it does demonstrate that the native production of this allomorph in vivo can be accomplished. The production and identification of strains with high rates of sustained cellulose II production (and therefore industrial utility) has been established as a reasonable possibility.

The desirable properties of cellulose II derived by chemical treatment from typical cotton fiber cellulose I have already been mentioned. There are other advantages of in vivo production of cellulose II by *A. xylinum* (or similar organisms) as compared to current chemical production methods. As produced by *Acetobacter* mutants of the present invention, no chemical treatment is needed to convert cellulose I to cellulose II. In addition, unlike the wild type which may lose its ability to form cellulose upon prolonged agitated culture (including many conventional fermenters), the mutants described here appear to retain the ability to make cellulose II under these conditions. In addition, because the product does not consist of extended ribbons (i.e., there is no pellicle), it would be relatively easily to transfer the product to and from fermentation, cleaning and processing vessels. Finally, it seems reasonable to expect that mixed cultures producing both cellulose I and cellulose II (or even other allomorphs) could be produced.

SUMMARY OF THE INVENTION

The present invention involves a process for screening for and isolating spontaneously occurring or induced cellulose II-producing microorganisms. The cellulose II-producing variants of the present invention were selected by initially screening for altered colony morphology on agar plates followed by growth in liquid medium to screen for variants deficient in pellicle formation. The cellulose produced by variants was in the form of small rodlets, rather than long ribbons, and no pellicle formation was associated. The process comprises a series of steps in various embodiments. Initially, cellulose-producing microorganisms from a first culture were plated out on a nutrient agar plate. The nutrient agar plate was then incubated to facilitate formation of colonies from single microorganisms. Liquid nutrient medium was then inoculated with microorganisms from single colonies having a smooth morphology, as compared to the usual rough colony configuration. The inoculated samples were then incubated under conditions favorable to microorganism proliferation and pellicle formation. From these incubated samples were selected microorganisms which, after a suitable cultivation period, had proliferated but not formed a pellicle. Said microorganisms produced cellulose II as contracted with the cellulose I produced normal by pellicle-forming organisms.

In additional modes of screening, cellulose-producing microorganisms from a first culture were plated out on a first nutrient agar plate and the plate incubated to facilitate formation of colonies from a single microorganism. Colonies with a smooth morphology were then selected from the nutrient agar plate and microorganisms therefrom cultivated to produce cellulose. Cellulose products of the cultivated microorganisms were then purified and subjected to x-ray diffraction and resultant d-spacings observed. Microorganisms were identified which produced cellulose giving x-ray diffraction spacings characteristics of cellulose II. The cellulose products of cultivated microorganisms may alternatively be subjected to electron microscopy to observe the ultrastructural morphology of the cellulose product. Microorganisms which produce electron microscopically observable rodlets characteristic of cellulose II could then be selected.

In any of the above-described methods of screening, selecting and isolating microorganisms which produce cellulose II, the first culture may be treated with a mutagen, for example, nitrosoguanidine. Such a mutagen greatly increases the frequency of smooth colony appearance. In another instance, when the first culture of cellulose producing microorganism is grown as a shaken liquid culture, rather than the more usual static pellicle-forming culture, the culture conditions may enhance the frequency of smooth colony-producing microorganisms.

In the above-described process, the microorganism is preferably a prokaryote, although conceivably eukaryotic cells such as those of algae could be utilized. The most preferred prokaryotic organism is classified as an *Acetobacter*, most preferably as an *Acetobacter xylinum*, an *Acetobacter hansenii*, *Acetobacter pasteurianus* or *Acetobacter aceti*.

BRIEF DESCRIPTION OF THE FIGURES

FIG. 1. Crystallites of cellulose are composed of regularly packed polymer strands of glucose. These strands, called glucan chains, have polarity. One end is referred to as a reducing end, and the other, the nonreducing end. In this diagram, the reducing end is shown as an arrowhead. FIG. 1A shows the most widely accepted model of cellulose I (native cellulose) has all the reducing ends of a crystallite oriented in the same direction. This is called "parallel" orientation. FIG. 1B shows what most researchers believe, that the reducing ends within a cellulose II crystallite have random polarity (an "antiparallel" arrangement).

FIG. 2. Some of the allomorphs of cellulose can be converted to other crystalline forms. This diagram shows some of these possible conversions. Note that the conversion from cellulose I to cellulose II is thought to be irreversible.

FIG. 3. Colony morphology of cells grown on agar plates for about 30 days. FIG. 3A1 shows colonies of wild type cells (strain NQ5). FIG. 3A2 (3B2 and 3C2) show corresponding colonies, at higher magnification. FIGS. 3B-3C shows mutant strains derived from the NQ5 parent, FIG. 3B1 and 3B2 NQ5-19 and FIG. 3C1 and 3C2 Pel-A. The uneven, rough texture of the wild type colonies is easily distinguished from the spreading, relatively smooth mutant cells. Colony variants, such as those shown, often are composed of cells that synthesize cellulose II.

FIG. 4. Light microscopy of cellulose II produced by variant NQ5-19. FIG. 4A shows a phase contrast light micrograph of a floc (small aggregate). (Note amorphous gray material (thought to be cellulose II) between the rod shaped cells) FIG. 4B shows the same floc stained with the cellulose binding fluorescent dye Tinopal LPW and viewed under UV illumination. Cells are enmeshed in brightly stained material. An X-ray diffraction patterns of such material are equivalent to those of cellulose II standards.

FIG. 5. X-ray diffraction powder patterns of cellulose.

FIG. 7. Negative staining electron microscopy of *Acetobacter* cellulose.

DESCRIPTION OF THE PREFERRED EMBODIMENTS

Organism and Culture Conditions

Figure 5A:
FIG. 5A shows that for Cellulose I (native cellulose) produced by strain NQ5.
Figure 5B:
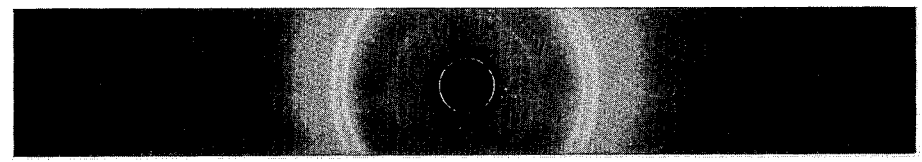
FIG. 5B-5D show patterns for cellulose II synthesized by mutants (strains NQ5-4, Pel-A, and NQ5-19, respectively).
Figure 5C:
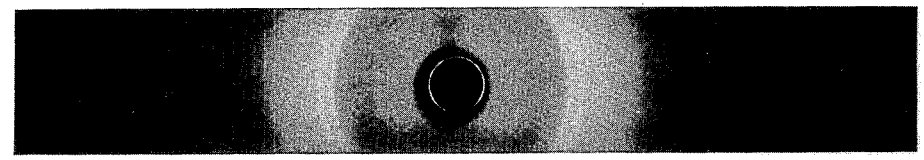
Figure 5D:
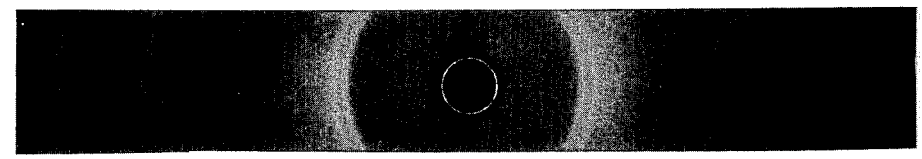
Figure 5E:
FIG. 5E shows the pattern for microcrystalline rayon, a standard cellulose II. The d-spacings (placement of diffraction maxima) of variants cells are essentially identical to cellulose II standards.

Two parent strains of *A. xylinum* were used for our studies: *A. xylinum* strain ATCC 53582 (hereafter referred to as NQ5) and *A.xylinum* strain ATCC 23769. Cells were cultured in "SH medium" described by Hestrin and Schramm (1954) at 28° C. Liquid shake cultures were agitated on an orbital shaker at 100 rpm. Stock cultures of all strains were maintained on SH medium solidified with 1.5% agar.

Mutagenesis and Colony Screening

Nitrosoguanidine Mutagenesis

A rifampicin resistant derivative of *A. xylinum* strain NQ5 was grown in liquid SH medium from a single colony. After 5 days of culture at 28° C. on an orbital shaker, a larger number of spherical pellicles were obtained. (In contrast to the flat pellicles produced by static cultures, shaken cultures form spherical pellicles (Schramm and Hestrin, 1954)). Cellulase (Novo Celluclast, 1200 1/100 ml) was added directly to the culture medium just after pellicle formation had begun and the cells were allowed to grow for one more day. Cellulase treatment hydrolyzed the pellicle and facilitated the isolation of large numbers of viable cells (Dillingham, et al. 1961; Brown, 1986). Five ml of the bacterial culture was passed through a syringe and the cells collected on a 0.22 m nitrocellulose filter. The cells were washed on the filter by passing 10 ml of 50 mM phosphate buffer, pH 6.0, and released from the filter by vortexing in 1 ml of the same buffer. The filter was removed from the tube and nitrosoguanidine (N-Methyl-N,-nitro-N-nitrosoguanidine, abbreviated NTG) was added. The cells were incubated on a shaker at 28° C. for 30 minutes after which 10 ml of buffer was added. The cells were incubated on a shaker at 28° C. for 30 minutes after which 10 ml of buffer was added to the trube and the cells collected by passing the suspension through a nitrocellulose filter. Cells on the filter Were washed with 10 ml of buffer and finally suspended in 5 ml SH medium. Cells were incubated on a shaker at 28° C. for 4 hours after which they were plated on SH agar at different dilutions.

Different concentrations of NTG (0, 10, 20, 80 and 100 g/ml) were tested for cell mortality and production of smooth colonies on agar plates.

Screening

In liquid SH medium, wild type *A. xylinum* strain NQ5 forms a thick pellicle at the surface of the medium; when grown on agar plates, the strain produces rough, convex colonies, which are somewhat leathery. Colonies obtained following various treatments were screened on SH agar plates for morphological variation, especially the appearance of smooth colonies. Rough colonies characteristic of wild type cellulose I-producing *Acetobacter* and smooth colonies characteristic of *Acetobacter* likely to be producing cellulose II are shown in FIG. 3.

The smooth colonies were then inoculated in liquid SH medium to screen for pellicle formation. Among the smooth colonies, a number of isolates did not form a pellicle, but instead formed small flocs. Such isolates are referred to as pellicle minus (pel-).

Isolation of Product

Although many procedures for the purification of cellulose are known, the following protocol was developed to circumvent the use of cleaning agents (e.g., NaOH) which could potentially convert low crystallinity cellulose I into cellulose II. Cells and associated cellulose were collected from liquid SH medium by centrifugation at 10,000×g. The pellet was resuspended in 10 mM Tris, 1 mM EDTA, pH 8.0 containing 1 mg/ml lysozyme. The resultant mixture was incubated at 37° C. overnight. Insoluble material was collected by centrifugation, the pellet resuspended in 2% SDS and heated in a boiling water bath. Remaining insoluble material was washed repeatedly with distilled water.

Product Characterization

Product Solubility

The material isolated from pel- strains was tested for insolubility in boiling water, 2% SDS and in boiling 1 N NaOH. It was also tested for solubility in the cellulose solvent Cadoxen (for preparation, see Henley, 1961).

Cellulase Sensitivity

Cell flocs (aggregates of cells and cellulose) and cellulose purified from mutant cell cultures as described, were treated with 1% cellulase (Novo Celluclast) in acetate buffer, pH 4.8 at 36° C. Flocs were scored for dispersion and, in some cases, dissolution was monitored by light microscopy or by a glucose assay (Sigma Chemical Co.).

Light and Electron Microscopy

Cells and cellulose were examined and photographed for light microscopy on an Olympus BHT microscope equipped for UV epifluorescence and phase contrast. Samples were stained by adding one drop or less of a saturated solution of Tinopal or Calcofluor mixed in SH medium to several ml of cell solution. (The precipitation of Tinopal and Calcofluor in SH medium is apparently due to the citric acid. Precipitates are removed before staining by centrifugation.

Cellulose was prepared for electron microscopy by placing the aqueous sample on a grid, wicking off the excess water just prior to staining. Samples were examined with a Philips EM 420 electron microscope operating at 80 kV.

X-Ray Diffraction

X-ray powder diffraction patterns were produced using a Philips PW1729 x-ray generator and a Debye-Scherrer camera 114.83 mm diameter. Samples were packed into glass capillary tubes (inner diameter of 0.3 or 0.5 mm). Dry samples were run in unsealed capillaries at ambient room humidity (ca. 60%), while tubes containing wet samples were sealed by heating the open end in a flame. Diffraction patterns were recorded at 35 kV and 25 mA using Ni filtered Cu k radiation on Kodak DEF X-ray film. Exposure times were approximately 45 minutes.

Wild type *Acetobacter* cellulose (NQ5 strain) was used as a standard for cellulose I and rayon obtained from Unitaka Co., Japan was the standard for cellulose II.

Powder diffraction negatives were scanned using the gel scanning attachment of a Beckman DU 8B spectrophotometer at 480 nm. d-spacings were determined from these densitometer traces.

HPLC Neutral Sugar Analysis

The neutral sugar composition of cellulose from three NTG mutants (NQ5-19, NQ5-20-1, and NG7) was studied by High Performance Liquid Chromatography (HPLC). Wild type *A. xylinum* cellulose, purified by the same procedure, was also run for comparison. One to 2 mg of sample were hydrolyzed with vigorous stirring in 0.2 ml of fuming HCl for 10 minutes at 4° C., then removed to room temperature (25° C.) for an additional 15 minutes. Each sample was diluted with 1 ml of $H_2O$. At this point, 200 g of glucose, xylose, galactose, rhamnose, mannose and inositol was added to a separate vial upon dilution of the fuming HCl. The solutions were vortexed and dried under a stream of dry nitrogen at 40° C. Three 70% ethanol assists were used to remove any residual HCl. One ml of 2N trifluoracetic acid (TFA) was added, the specimen vials evacuated, and the hydrolysis continued for three hours at 121° C. Samples were removed from heat and dried as described above. Specimens were then dissolved in 400 1 $H_2O$, filtered through 0.22 m filters into a 1.5 ml plastic centrifuge tube and again dried under a stream of dry $N_2$ at 40° C. Samples were rehydrated with 100 1 $H_2O$ and 10 1 were injected on a BioRad HPX 27P neutral sugar column operated at 85° C. on a Beckman HPLC module. Water was used as the solvent. Sugars were detected using an Altex refractive index detector and attached to a Hewlett Packard Integrator.

Determination of Degree of Polymerization

Degree of polymerization (DP) determinations for cellulose (a cellulose product from Sigma Chemical), rayon (Unitaka, Osaka, Japan), NQ5-0-1, and NG7 were determined by high performance gel permeation chromatography (HPGPC). Samples were first nitrated by the method of Green (1963), and then dissolved in tetrahydrofuran (THF) at a concentration of 3 mg/ml and filtered. 200 1 samples were then injected on a Waters HPGPC system with a series of 5 Styragel columns operating at a flow rate of 1.9 ml/min and a chart speed of 0.5 in/min. Elution of samples was detected using a refractive index detector. The system was calibrated with a series of polystyrene molecular weight standards. Complete nitration was assumed and end effects were not considered. Values were adjusted based on the actual retention time of the 200,000 MW polystyrene standard.

Isolation of Microorganisms Producing Cellulose II

Microorganisms from various cultures with and without mutagen were plated out on nutrient agar plates and colonies with abnormal phenotype noted.

In our studies, smooth colony non-pellicle forming derivatives from wild type *A. xylinum* were obtained from spontaneously occurring variants and by treatment with the mutagen NTG. Following NTG mutagenesis, cells plated on SH agar plates were screened for colony development after 9 to 13 days. From a total of 8000 colonies screened in one experiment, 50 colonies appeared smooth and shiny as distinct from the wild type which were rough. At this stage the frequency of smooth colony appearance was $6.25 \times 10^{-3}$. All colonies patched grew on SH plus rifampicin plates suggesting that they were derived form the parent strain and not a contaminant. When cells from 37 of these smooth colonies were inoculated in liquid SH medium, 15 colonies immediately formed pellicles. On prolonged incubation, 7 more formed pellicles. The remaining colonies did not give rise to a pellicle for the duration of the experiment. It is from these colonies that further experiments to characterize and isolate the product was undertaken. A plasmid analysis from these isolates showed no visible changes from the wild type. These variants are referred to as pel- strains. Such colonies typically fluoresce on plates containing the cellulose binding fluorochrome Tinopal. Cells from these colonies stained with Tinopal and observed under the fluorescence microscope showed a characteristic fluorescence (FIG. 4(B)). This suggested that a Tinopal-positive product was being formed. However, because Tinopal staining may be nonspecific, this is not conclusive evidence for the presence of cellulose.

Table 2 shows a list of strains used in these investigations.

TABLE 2
LIST OF STRAINS

| Strain | Origin | Colony Characteristics |
|---|---|---|
| (Parent Strain) | | |
| NQ5 (ATCC 53582) | Wild type | Rough colony; pel+* Rifampicin resistant |
| (Strains Derived from NQ5) | | |
| NQ5-0-1 | Spontaneous | Smooth colony, pel− |
| NQ5-0-2 | Spontaneous | Smooth colony, pel− |
| NQ5-A | Shake culture | Smooth colony, pel− |
| NQ5-B | Shake culture | Smooth colony, pel− |
| NQ5-C | Shake culture | Smooth colony, pel− |
| NQ5-D | Shake culture | Smooth colony, pel− |
| NG7 | NTG | Smooth colony, pel− |
| NQ5-1 | 10 g/ml NTG | Smooth colony, pel− |
| NQ5-3 | 10 g/ml NTG | Smooth colony, pel− |
| NQ5-4 | 10 g/ml NTG | Smooth colony, pel− |
| NQ5-8 | 10 g/ml NTG | Smooth colony, pel− |
| NQ5-9 | 10 g/ml NTG | Smooth colony, pel− |
| NQ5-14 | 10 g/ml NTG | Smooth colony, pel− |
| NQ5-17 | 10 g/ml NTG | Smooth colony, pel− |
| NQ5-19 | 10 g/ml NTG | Smooth colony, pel− |
| NQ5-21 | 10 g/ml NTG | Smooth colony, pel− |
| NQ5-22 | 10 g/ml NTG | Smooth colony, pel− |
| NQ5-24 | 10 g/ml NTG | Smooth colony, pel− |
| NQ5-25 | 10 g/ml NTG | Smooth colony, pel− |
| NQ5-27 | 10 g/ml NTG | Smooth colony, pel− |
| NQ5-31 | 10 g/ml NTG | Smooth colony, pel− |
| NQ5-20-1 | 20 g/ml NTG | Smooth colony, pel− |
| NQ5-80-1 | 80 g/ml NTG | Smooth colony, pel− |
| (Strains Derived from ATCC 23769) | | |
| ATCC 23769-0-1 | Spontaneous | Smooth colony, pel− |

*−pel+ refers to the pellicle-forming strains and pel− refers to the non-pellicle forming phenotype)

Characterization of Product From Smooth Colony Non-Pellicle-Forming Cells

When grown in liquid SH medium, pel- cells formed flocs that settled when shaking was stopped. A product isolated from these cultures (as described in materials and methods) was examined by x-ray diffraction. The diffraction pattern obtained from freeze-dried material was typical of the allomorph cellulose II. (FIG. 5). It has been reported that amorphous (non-crystalline) cellulose can crystallize to form cellulose II when dried from a polar environment such as water (Bertran and Dale, 1985). In order to determine if this was the case with the product of pel- cultures, we employed the technique of solvent exchange drying. In this procedure, water is first exchanged for ethanol and then for n-pentane. The product can then be dried from the nonpolar environment without risk of dehydration induced crystallization. The x-ray diffraction pattern from such material gives the three principle reflections of cellulose II. Thus, the native form of cellulose produced by pel- Acetobacter strains was crystalline cellulose II. Since the same x-ray diffraction pattern was observed following freeze-drying from water, freeze-drying was routinely used to dry the product obtained from other strains. The d spacings obtained from different strains are given in Table 3. In each pel- variant examined to date, material can be recovered by the method described that gives the x-ray diffraction pattern of cellulose II.

TABLE 3
d-SPACINGS OF CELLULOSE SAMPLES

| | d-SPACINGS (Å) | | |
|---|---|---|---|
| Sample | (002) | (10-1) | (101) |
| NQ5-wt (Cellulose I standard) | 3.95, | 5.46, | 5.96 |
| RAYON (Cellulose II standard) | 4.06, | 4.41, | 7.34 |
| NQ5-0-1 | 4.11, | 4.45, | 7.46 |
| NQ5-0-2 | 4.05, | 4.43, | 7.34 |
| NQ5-1 | 4.09, | 4.43, | 7.37 |
| NQ5-2 | 4.06, | 4.43, | 7.40 |
| NQ5-3 | 4.08, | 4.45, | 7.46 |
| NQ5-4 | 4.09, | 4.45, | 7.37 |
| NQ5-5 | 4.09, | 4.45, | 7.37 |
| NQ5-19 | 4.08, | 4.43, | 7.40 |

Figure 6:
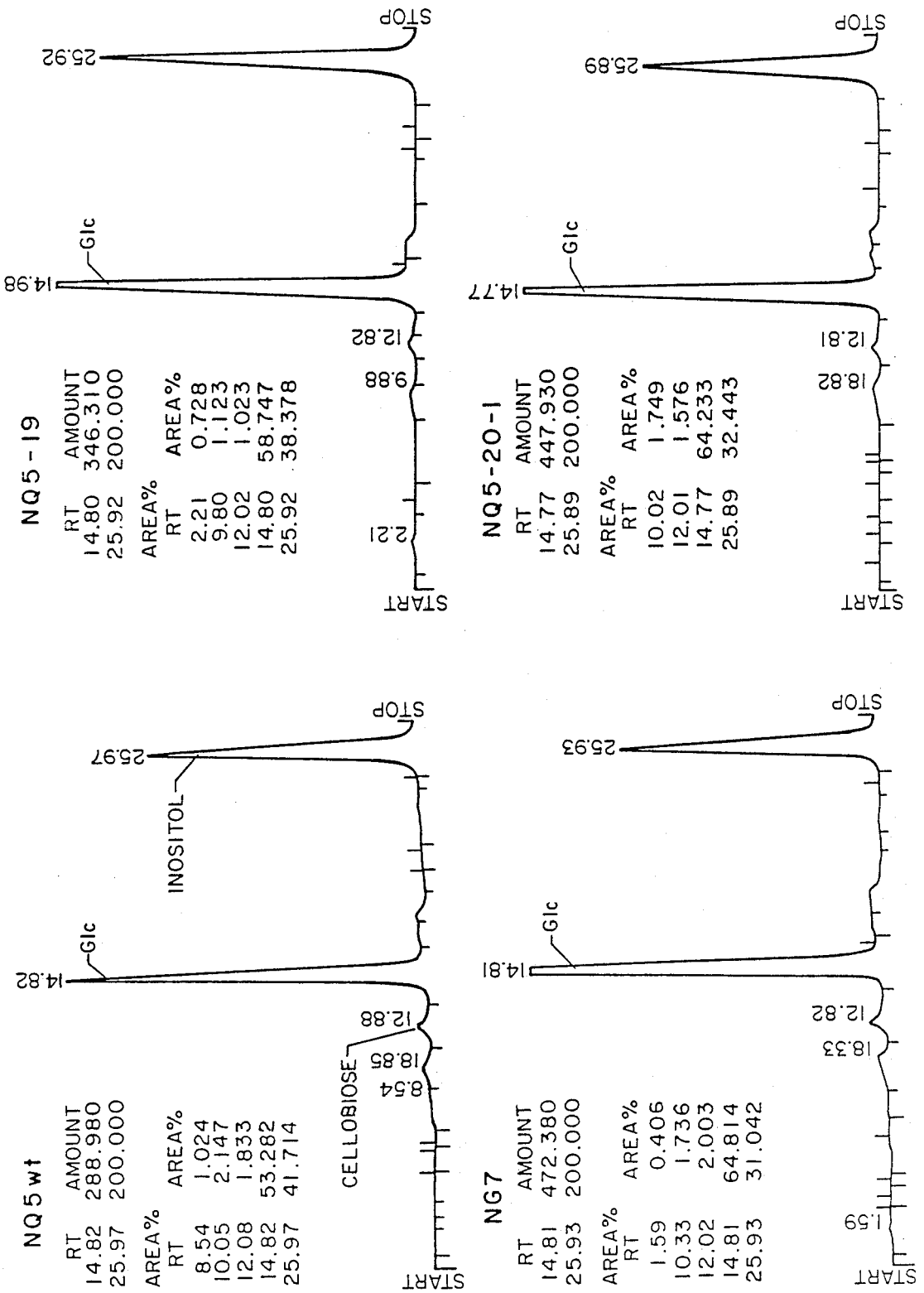
FIG. 6. High performance liquid chromatogram (HPLC chromatogram) of hydrolysates of cellulose produced by NQ5, the wild type strain, variant strains NQ5-19, NG7 and NQ5-20-1. All show a single major monosaccharide peak co-migrating with glucose standards. These results are consistent with the presence of cellulose II in mutant cells.

In order to confirm that the material isolated from pel- strains was indeed cellulose, a neutral sugar analysis was carried out by high performance liquid chromatography (HPLC). Under the hydrolysis conditions employed, the chromatograms of pel- strains were identical to wild type NQ5 cellulose run under the same conditions (FIG. 6). In each case, the only monosaccharide observed was glucose. A small peak co-eluting with cellobiose was also observed that results from the incomplete hydrolysis of cellulose under the conditions employed.

Further evidence for the cellulosic nature of the pel- product was supplied by its complete solubility in the cellulose solvent Cadoxen and by its complete dissolution by cellulase enzymes. The cellulase used in our work ("Novo Celluclast") was an enzyme mixture containing an endo- and exo-glucanase, a cellobiohydrolase and a cellobiase. Such enzymes are specific for -1,4 linked glucans of cellulose. When pel- product was subjected to exhaustive enzymatic hydrolysis, the amount of glucose liberated was measured using a glucose oxidase assay. Essentially the entire weight of the product could be accounted for by the amount of glucose produced by enzymatic hydrolysis.

It has been reported that x-ray diffraction patterns resembling cellulose II can also be obtained from extremely low molecular weight oligomers of 1,4-glucan (Robinson and preston, 1972). Such small compounds are not typically considered to be cellulosic, thus it is important to establish that the product is a polymer of at least moderate length. The degree of polymerization (DP, a measure of the average number of monomer units present in the polymer) of the product was determined by high performance gel permeation chromatography (HPGPC) of nitrated samples of pel- product. The approximately weight average DP determined were as follows: cellulose, 2,100; rayon 1,200; NQ5-0-1, 570; and NG7, 670.

Morphological Characterization

The morphology of pel- variant cells and the cellulose they produce was examined by both light and electron microscopy. When samples of pel- cultures were stained with Tinopal LPW and observed using epifluorescence light microscopy, characteristic fluorescent blue flocs were observed (FIG. 4(B)). These flocs contain both cells and a fluffy phase dense material (presumably cellulose). Individual cells do not fluoresce, or do so only slightly. The product isolated from pel- cultures (as described in materials and methods) fluoresced brightly.

Figure 7A:
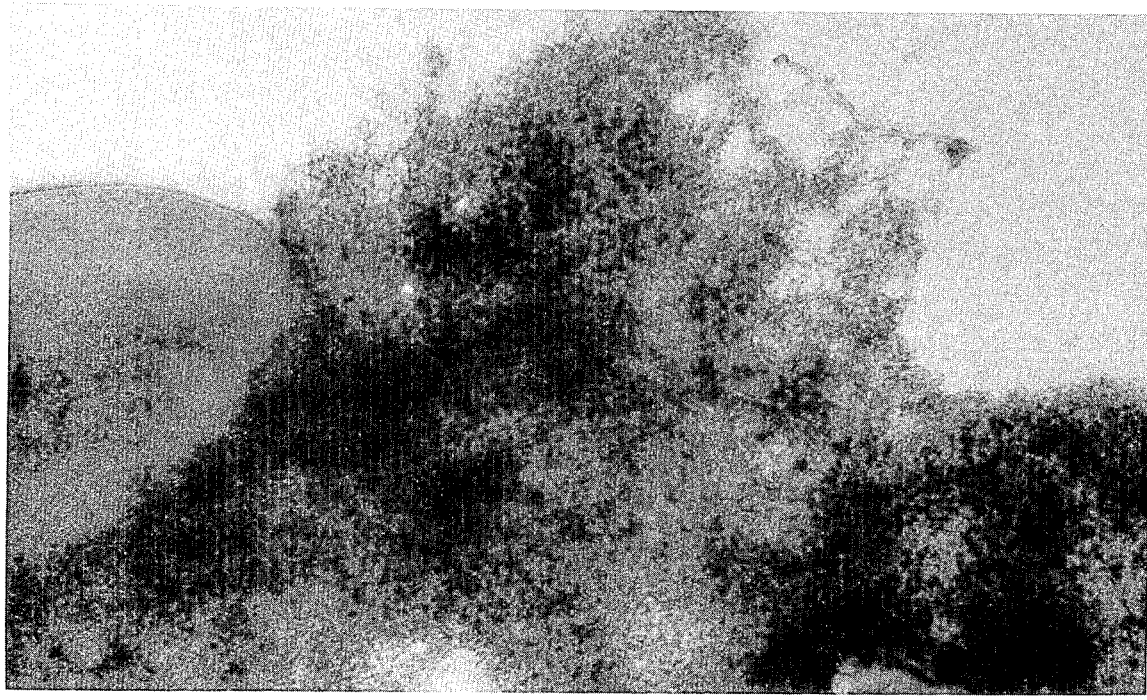
FIG. 7A shows cellulose II produced by the variant strain NQ5-19. This material is composed of small rodlets collected into mats. A portion of a cell is visible at the left side of the figure.
Figure 7B:
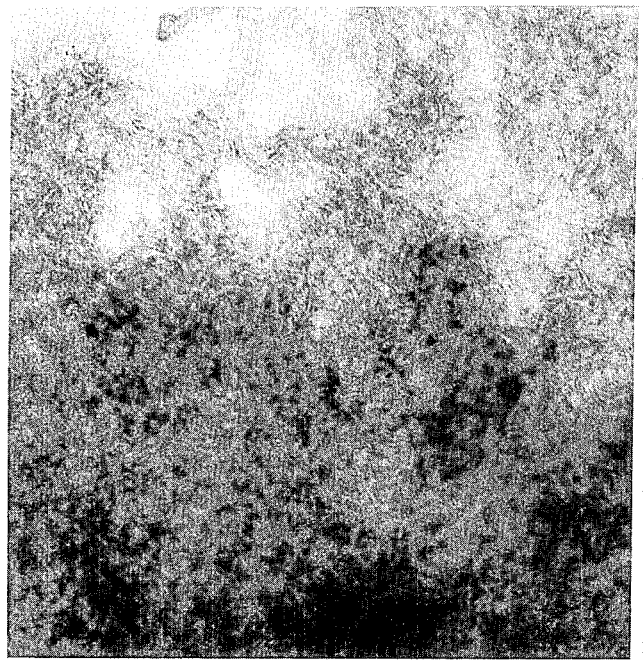
FIG. 7B shows higher magnification of cellulose II produced by strain NQ5-19.
Figure 7C:
FIG. 7C shows a ribbon of cellulose I produced by the wild type strain NQ5. Such ribbons are generally very long and compact.

When cellulose purified from pel- variants was examined by negative staining electron microscopy, it appeared to be composed of numerous short rodlets (FIG. 7). This morphology differed dramatically from the flat twisting ribbons of cellulose I produced by wild type cultures, but is similar to the morphology of cellulose II regenerated from solution (Kolpak and Blackwell 1978) and in vitro cellulose II (Lin and Brown, personal communication).

Growth Characteristics

Figure 8:
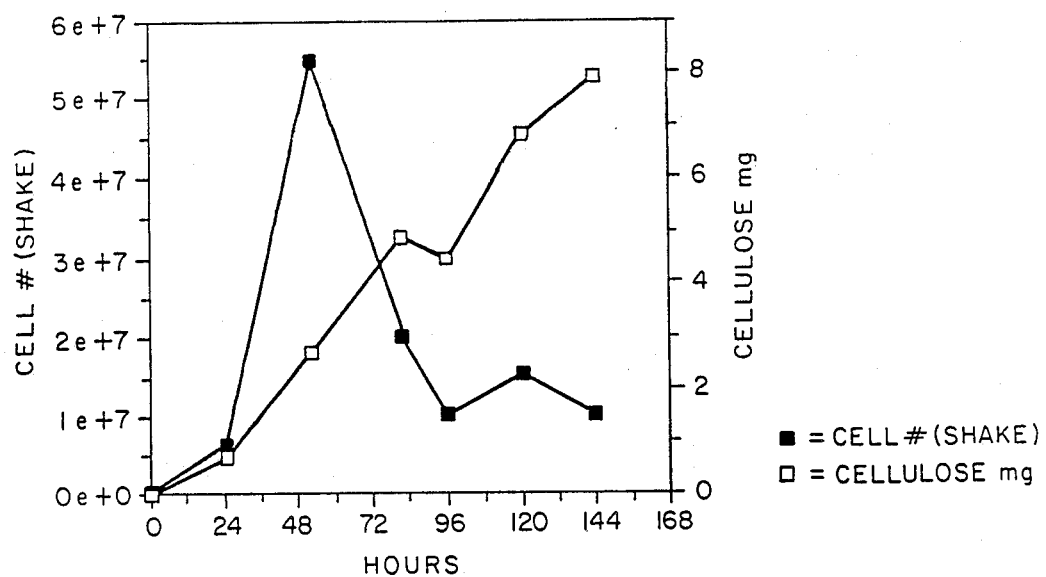
FIG. 8. Graph of cell growth and cellulose production kinetics for the mutant strain NQ5-19. The rate of cellulose production in wild type cells (not shown) is substantially higher.

Generally, when cells are inoculated from SH agar plates into shaken liquid SH medium, flocs visible with the unaided eye appear within the first few days of culture. At this stage, the medium is clear indicating that relatively few free single cells are present. However, upon prolonged culture, these flocs disappear and the medium becomes turbid due to many free single cells. These cells are distinct in that they are greatly elongated relative to those observed immediately after inoculation. When such elongated cells were treated with lysozyme and EDTA to remove their walls, the spheroplasts formed were quite large indicating the that the long cells were whole single cells rather than an undissociated chain of many cells. Growth kinetics of the NQ5-19 strain grown in a 200 ml SH shake culture are shown in FIG. 8. This growth pattern is similar to the wild type *Acetobacter*, although much less cellulose is produced. The following list of references is incorporated by reference herein for the reasons cited.

Bertran, M. S. and B. E. Dale. 1985. Enzymatic hydrolysis and recrystallization behavior of initially amorphous cellulose. Biotechnol. Bioeng. 27:177–181.

Blackwell, J. and R. H. Marchessault. 1971. Investigations of the structure of cellulose and its derivatives. A. Infrared spectroscopy. In: Cellulose and Cellulose Derivatives, pt. IV. N. M. Bikales and L. Segal, eds. Wiley Interscience, New York, London, Sydney and Toronto.

Blanton, R. L. and H. D. Chanzy. 1985. Cellulose detected in the stalks of *Protostelium irregularis* (Eumycetozoea). J. Protozool. 32(4): 740-741.

Brown Jr., R. M., J. H. M. Wilson and C. Richardson. 1976. Cellulose biosynthesis in *Acetobacter xylinum*: Visualization of the site of synthesis and direct measurement of the in vivo process. Proc. Nat. Acad. Sci. USA. 73:4565–4569.

Brown Jr., R. M., C. H. Haigler, J. Suttie, E. Roberts, C. Smith, T. Itoh and K. Cooper. 1983. The biosynthesis and degradation of cellulose. J. Appl. Polymer Symp. 37: 33–78.

Brown, R. M., Jr. 1986. patent application Ser. #06 900 384.

Bureau, T. E. and R. M. Brown, Jr. 1987. In Vitro synthesis of cellulose II from a cytoplasmic membrane fraction of *Acetobacter xylinum*. Proc. Nat. Acad. Sci. USA 84: 6985–6989.

Canale-Parola, E., R. Borasky and R. S. Wolfe, 1961. Studies on *Sarcina ventriculi*. III. Localization of cellulose. J. Bacteriol. 8:311–318.

Canale-Parola, E. and R. S. Wolfe. 1964. Synthesis of cellulose by *Sarcina ventriculi*. Biochim. Biophys. Acta 82: 403–405.

Creedy, A. E., P. Jowett and T. K. Walker. 1954. Formation of D-cellobiose from starch and from other substrates in an *Acetobacter* species. Chem. Ind. (Rev.) 73:1279.

Cronshaw, J., A. Myers and R. D. Preston. 1958. A chemical and physical investigation of the cell walls of some marine algae. Biochim. Biophys. Acta 27:89–103.

Deinema, M. H. and L. P. T. M. Zevenhuizen. 1971. Formation of cellulose fibrils by gram-negative bacteria and their role in flocculation. Arch. Mikrobiol. 78:42–57.

De Ley, J. 1961. Comparative carbohydrate metabolism and a proposal for a phylogenetic relationship of the acetic acid bacteria. J. Gen. Microbiol. 24:31–50.

De Ley, J., M. Gillis and J. Swings. 1984. Family VI. Acetobacteraceae. In: "Bergey's Manual of Systematic Bacteriology". v. 1, (N. R. Krieg and J. G. Holt, eds.) Williams and Wilkins, Baltimore and London. pp. 267–274.

Dillingham, E. O., A. G. Jose and D. T. Knuth. (1961) Cellulose and cellulose-free cell production by *Aceto-

*bacter xylinum.* (Abstract). Bact. Proc. 61st Ann. Meting, p. 67.

Dodson, J. R. and J. M. Aronson. 1978. Cell wall composition of *Enteromorpha intestinalis.* Botanica Marina 21:241–246.

Ellefsen, Ø. and B. A. Tønnesen. 1971. C.2. Polymorphic Forms. In: Cellulose and Cellulose Derivatives, pt. IV. N. M. Bikales and L. Segal, eds. Wiley Interscience, New York, London, Sydney and Toronto.

Forge, A. 1977. Electron microscopy of a non-pellicle-forming strain of *Acetobacter xylinum.* Ann. Bot. 41:455–460.

Frei, E. and R. D. Preston. 1961. Variants in the structural polysaccharides of algal cell walls. Nature 192:939–943.

Frei, E. and R. D. Preston. 1963. Clay minerals and the cell walls of seaweeds. Proc. Leeds Phil. Lit. Soc. (Scientific Section) 9(4):101–111.

French, A. 1985. Physical and theoretical methods for determining the supramolecular structure of cellulose. In: Cellulose Chemistry and Its Applications (T. P. Nevell and S. H. Zeronian, eds.) Ellis Horwood Ltd., Chichester.

Frey-Wyssling, A. 1976. The Plant Cell Wall. Gerbruder Borntraeger, Berlin and Stutgart.

Gezelius, K. 1959. The ultrastructure of cells and cellulose membranes in Acrasiae. Exp. Cell Res. 18:425–453.

Gezelius, K. and B. G. Rånby. 1957. Morphology and fine structure of the slime mold *Dictyostelium discoidium.* Exp. Cell Res. 12:265–289.

Green, J. 1963. Nitration. In: "Methods in Carbohydrate Chemistry" v. III. R. L. Whistler, ed. Academic Press, New York.

Haigler, C. and M. Benziman. 1982. Biogenesis of cellulose I microfibrils occurs by cell-directed self assembly in *Acetobacter xylinum.* In: Cellulose and Other Natural Polymer Systems: Biogenesis, Structure and Degradation. R. M. Brown Jr., ed. Plenum Press, New York and London.

Henley, D. 1961. A macromolecular study of cellulose in the solvent Cadoxen. Arkiv Kemi 18:327–391.

Hestrin S. and M. Schramm. 1954. Synthesis of cellulose by Acetobacter xylinum. II. Preparation of freeze-dried cells capable of polymerizing glucose to cellulose. Bioch. J. 58:345–352.

Hieta, K., S. Kuga and M. Usuda. 1984. Electron staining of reducing ends evidences a parallel chain structure in *Valonia* cellulose. Biopolymers 23:1807.

Horii, F., A. Hirai and R. Kitamaru. 1987. Cross-polarization-magic angle spinning carbon-13 NMR approach to the structural analysis of cellulose. In: The Structure of Cellulose: Characterization of the Solid State (A.C.S. Symposium Series 340). R. H. Atalla, ed. American Chemical Society, Washington, D.C.

Huizing, H. J., H. Reitma and J. H. Sietsma. 1979. Cell wall constituents of several siphonous green algae in relation to morphology and taxonomy. Br. Phycol. J. 14:25–32.

Joseph, M. L. 1977. Introductory Textile Science, 3rd Edition. Holt, Rinehart and Winston, New York, Chicago, San Francisco, Atlanta, Dallas, Montreal, Toronto, London, Sydney.

Kolpak, F. J. and J. Blackwell. 1978. The morphology of regenerated cellulose. Textile Res. J. 48:458–467.

Kulshreshtha, A. K. 1979. A review of the literature on the formation of cellulose IV, its structure, and its significance in the technology of rayon manufacture. J. Textile Inst. 70(1):13–18.

Meyer, K. H. and H. Mark. 1928. Uber den Bau des krystallisierten Anteils der Cellulose. Ber. Deutschen Chem. Gesel. 61:593–614.

Moncrieff, R. W. 1975. Man-Made Fibers. Newnes-Butterworths London and Boston.

Muhlethaler, K. 1956. Electron microscopic study of the slime mold *Dictyostelium discoidium.* Am. J. Bot. 43:673–678.

Myers, A. and R. D. Preston. 1959. Fine structure in the Red algae. II. The structure of the cell wall of Rhodymenia palmata. Proc. Roy. Soc. B. 150:447–455.

Myers, A., R. D. Preston and G. W. Ripley. 1955. Fine structure in the Red algae. II. The structure of the cell wall of *Rhodymenia palmata.* Proc. Roy. Soc. B. 150:447–455.

Myers, A., R. D. Preston and G. W. Ripley. 1955. Fine structure in the Red Algae. I. X-ray and electron microscopic investigation of *Griffithsia flosculosa.* Proc. Roy. Soc. B 144:450–459.

Nicolai, E. and R. D. Preston. 1952. Cell wall studies in he Chlorophyceae. I. A general survey of submicroscopic structure in filamentous species. Proc. Roy. Soc. B 140:244–274.

Preston, R. D. 1974. The Physical Biology of the Plant Cell Wall. Chapman and Hall, London.

Raper, K. B. and D. I. Fennell. 1952. Stalk formation in *Dictyostelium.* Bull. Torrey Bot. Club, 79(1):25–51.

Robinson, D. G. and R. D. Preston. 1972. Polysaccharide synthesis in Mung bean roots—An x-ray investigation. Biochim. Biophys. Acta 273:336–345.

Roelofsen, P. A. 1959. The Plant Cell Wall. Gebruder Borntraeger, Berlin-Nikolassee.

Roelofsen, P. A., V.ch. Dalitz and C. F. Wijnman. 1953. Constitution, submicroscopic structure and degree of crystallinity of the cell wall of *Halicystis osterhoutii.* Biochim. Biophys. Acta 11:344–352.

Sakthivel, A., A. F. Turbak and R. A. Young. 1987. Models for cellulose II: Mercerized and regenerated cellulose. TAPPI Proceedings. 1987 International Dissolving Pulps Congress.

Sarko. A 1978. What is the crystalline structure of cellulose? TAPPI 61:59–61.

Schell, J. and J. De Ley. 1962. Variability of acetic acid bacteria. Antonie va Leeuwenhoek 28: 445–465.

Schramm, M. and S. Hestrin. 1954. Factors affecting producing of cellulose at the air-liquid interface of a culture of *Acetobacter xylinum.* J. Gen. Microbiol. 11:123–129.

Shimwell, J. L. 1956. Transmutation of species in the genus *Acetobacter.* J. Inst. Brew. 62:339–343.

Shimwell, J. L. and J. C. Carr. 1960. Derivation of non-acetifying "quasi-Acetobacters" from a true *Acetobacter* strain and vice versa. Antonie van Leeuwenhoek 26:169.

Sisson, W. 1938. The existence of mercerized cellulose and its orientation in Halicystis as indicated by x-ray diffraction analysis. Science 87:350.

Sisson, W. 1941. Some x-ray observations regarding the membrane structure of Halicystis. Contr. Boyce Thomp. Inst. 12:31–44.

Sleytr, U. B. and A. W. Robards. 1977. Plastic deformation during freeze-cleavage: a review J. Microsc. 110(1):1–25.

Steel, R. and T. K. Walker. 1957. A comparative study of cellulose-producing cultures and celluloseless mutants of certain Acetobacter spp. J. Gen. Microbiol. 17:445–452.

Tripp, V. W. and C. M. Conrad. 1972. X-ray diffraction. In: "Instrumental Analysis of Cotton Cellulose and Modified Cotton Cellulose". R. T. O'Connor, ed. Marcel Dekker, Inc., New York Wiley, J. H. and R. H. Atalla. 1987. Raman spectra of celluloses. In: The Structure of Cellulose: Characterization of the Solid State (A.C.S. Symposium Series 340). R. H. Atalla, ed. American Chemical Society, Washington, D.C.

Valla, S. and J. Kjosbakken. 1982. Cellulose-negative mutants of *Acetobacter xylinum*. J. Gen. Microbiol. 128: 1401.

What is claimed is:

1. A process for selecting cellulose II-producing Acetobacter, the process comprising:
   plating out cellulose-producing Acetobacter from a first culture on a nutrient agar plate and incubating the plate to form microbial colonies from single Acetobacter, said colonies having visible configurations;
   inoculating samples of liquid nutrient medium with Acetobacter from colonies having a smooth configuration and incubating inoculated samples to facilitate Acetobacter proliferation, said incubating involving conditions which result in pellicle formation by Acetobacter which produce cellulose I; and
   selecting Acetobacter from samples exhibiting proliferation and cellulose production without pellicle formation, said selected Acetobacter producing cellulose II.

2. A process for isolating cellulose II-producing, Acetobacter the process comprising:
   plating out cellulose-producing Acetobacter from a first culture on a nutrient agar plate and incubating the plate to form colonies from single Acetobacter, said colonies having visible configurations;
   selecting colonies having a smooth configuration from the nutrient agar plate and cultivating Acetobacter therefrom to produce cellulose;
   subjecting cellulose produced by cultivated Acetobacter to means for distinguishing cellulose allomorphs;
   identifying cultures of cellulose-producing Acetobacter distinguished as producing cellulose II allomorph; and
   isolating Acetobacter producing cellulose II.

3. A process for isolating cellulose II-producing Acetobacter, the process comprising:
   plating out cellulose-producing Acetobacter from a first culture on a nutrient agar plate and incubating the plate to form colonies from single Acetobacter, said colonies having visible configurations;
   selecting colonies having a smooth configuration from the nutrient agar plate and cultivating Acetobacter therefrom to produce cellulose;
   defining cellulose products of cultivated Acetobacter by observing patterns obtained from said cellulose during subjection to x-ray diffraction, electron microscopy, electron diffraction, nuclear magnetic resonance spectroscopy or infrared spectroscopy;
   identifying cellulose giving patterns characteristic of cellulose II; and
   isolating Acetobacter producing cellulose II so identified.

4. A process for isolating cellulose II-producing Acetobacter, the process comprising:
   plating out cellulose-producing Acetobacter from a first culture on a nutrient agar plate and incubating the plate to facilitate formation of colonies form single Acetobacter;
   selecting colonies with a smooth configuration from the nutrient agar plate and cultivating Acetobacter therefrom to produce cellulose;
   subjecting cellulose products of cultivated Acetobacter to electron microscopy to observe ultrastructural morphology of the cellulose product; and
   identifying Acetobacter producing cellulose rodlets, said rodlets being characteristic of cellulose II; and
   isolating said identified Acetobacter.

5. A process for isolating cellulose II-producing Acetobacter, the process comprising:
   plating out cellulose-producing Acetobacter from a first culture on a nutrient agar plate and incubating the plate to form colonies from single Acetobacter, said colonies having visible configurations;
   selecting colonies having a smooth configuration from the nutrient agar plate and cultivating Acetobacter therefrom to produce cellulose;
   subjecting cellulose products of cultivated Acetobacter to x-ray diffraction to observe resultant d-spacings; and
   identifying Acetobacter producing cellulose giving x-ray diffraction d-spacings characteristic of cellulose II; and
   isolating said identified Acetobacter.

6. A process for producing cellulose II, the process comprising cultivating cellulose II-producing Acetobacter obtained by the process of claim 1, 2, 3, 4 or 5.

7. The process of claim 1, 2, 3, 4 or 5 wherein the first culture comprises a mutagen.

8. The process of claim 7 wherein the first culture comprises nitrosoguanidine.

9. The process of claim 1, 2, 3, 4 or 5 wherein the first culture is a shaken aerobic culture.

10. The process of claim 1, 2, 3, 4 or 5 wherein the Acetobacter from the first culture has American Type Culture Collection accession number ATCC 53582 or ATCC 23769.

11. The process of claim 1, 2, 3, 4 or 5 wherein the Acetobacter is classified as an Acetobacter xylinum.

12. The process of claim 1, 2, 3, 4 or 5 wherein the Acetobacter is classified as an Acetobacter hansenii.

13. The process of claim 1, 2, 3, 4 or 5 where the Acetobacter is classified as an Acetobacter pasteurianus.

14. The process of claim 1, 2, 3, 4 or 5 wherein the Acetobacter is classified as an Acetobacter aceti.

15. An isolated Acetobacter which produces cellulose II.

16. An isolated Acetobacteria which produces cellulose II, the strain being classified as an Acetobacter xylinum, Acetobacter hansenii, Acetobacter pasteurianus or Acetobacter aceti.

* * * * *